US012735381B2

(12) United States Patent
Jansen et al.

(10) Patent No.: US 12,735,381 B2
(45) Date of Patent: Sep. 15, 2026

(54) CARDANOL-BASED REACTIVE DILUENTS AND THEIR USE AND PREPARATION

(71) Applicant: Covestro (Netherlands) B.V., Geleen (NL)

(72) Inventors: Johan Franz Gradus Antonius Jansen, Geleen (NL); Simon Hsueh, New Taipei City (TW)

(73) Assignee: Covestro (Netherlands) B.V., Geleen (NL)

( * ) Notice: Subject to any disclaimer, the term of this patent is extended or adjusted under 35 U.S.C. 154(b) by 530 days.

(21) Appl. No.: 18/547,224

(22) PCT Filed: Feb. 25, 2022

(86) PCT No.: PCT/EP2022/054801
§ 371 (c)(1),
(2) Date: Aug. 21, 2023

(87) PCT Pub. No.: WO2022/180215
PCT Pub. Date: Sep. 1, 2022

(65) Prior Publication Data

US 2024/0317669 A1 Sep. 26, 2024

(30) Foreign Application Priority Data

Feb. 26, 2021 (EP) .................................... 21159740

(51) Int. Cl.

| | |
|---|---|
| ***C08F 2/46*** | (2006.01) |
| ***C07C 41/01*** | (2006.01) |
| ***C07C 41/20*** | (2006.01) |
| ***C07C 67/24*** | (2006.01) |
| ***C07C 69/54*** | (2006.01) |
| ***C08F 2/50*** | (2006.01) |
| ***C08G 18/34*** | (2006.01) |
| ***C08G 18/76*** | (2006.01) |
| ***C08G 61/04*** | (2006.01) |

(52) U.S. Cl.
CPC .............. *C07C 69/54* (2013.01); *C07C 41/01* (2013.01); *C07C 41/20* (2013.01); *C07C 67/24* (2013.01); *C08G 18/34* (2013.01); *C08G 18/7621* (2013.01)

(58) Field of Classification Search
CPC ......... C07C 41/20; C07C 41/01; C07C 69/54; C07C 67/24; C07C 67/08; C08G 18/7621; C08G 18/34
USPC ................ 522/64, 71, 1, 189, 184, 6; 520/1
See application file for complete search history.

(56) References Cited

U.S. PATENT DOCUMENTS

| | | | | |
|---|---|---|---|---|
| 3,046,226 A | 7/1962 | Sandberg et al. | | |
| 3,214,406 A | 10/1965 | Sandberg et al. | | |
| 2001/0033725 A1* | 10/2001 | Szum | C03C 25/1065 | 385/128 |
| 2015/0288027 A1 | 10/2015 | Lee et al. | | |
| 2022/0056286 A1* | 2/2022 | Hishinuma | C08F 2/44 | |

FOREIGN PATENT DOCUMENTS

| | | | | |
|---|---|---|---|---|
| CN | 107089914 A | | 8/2017 | |
| CN | 110483300 A | * | 11/2019 | C07C 69/54 |
| GB | 828496 A | | 2/1960 | |
| JP | 1986261368 | * | 5/1985 | |
| KR | 20100133681 A | | 12/2010 | |
| WO | WO-2020138132 A1 | * | 7/2020 | C09D 11/30 |

OTHER PUBLICATIONS

Tagakiuchi et al., JP 1986261368 Machine Translation, May 15, 1985 (Year: 1985).*
Guo et al., CN 110483300 Machine Translation, Nov. 22, 2019 (Year: 2019).*
"Properties and Applications of Acrylates", Acrylate Polymers for Advanced Applications, May 6, 2020, ISBN: 978-1-78985-184-7, pp. 35-46.
Advanced Organic Chemistry, 7th ed. (2013), chapter 15-11, pp. 902-909.
Comprehensive Organic Synthesis II, vol. 8 (2014), chapter 8.16, pp. 564-600.
International Search Report PCT/EP2022/054801, date of mailing: May 27, 2022, Authorized officer: Michiel Hacking.

* cited by examiner

*Primary Examiner* — Jessica Whiteley
(74) *Attorney, Agent, or Firm* — Donald R. Palladino

(57) ABSTRACT

Disclosed herein are compounds, including cardanol derivates based upon cashew nut shell liquid, of the following structure:

(Ia)

wherein $R_1$ is H or $CH_3$; $R_2$ is a $C_\gamma$ alkyl chain having a number of H atoms defined by the expression X (2Y+1); wherein Y is from 9 to 15 and X is from 0.93 to 1.0; $R_3$ is H or a $C_1$-$C_4$ alkyl chain, or H or $CH_3$; and m is from 3 to 9, or from 3 to 8. Also described and claimed are various compositions, including UV-curable compositions, containing the compounds elsewhere disclosed. Yet further described and claimed are methods of preparing the compounds, compositions, and/or mixtures elsewhere described and claimed.

22 Claims, No Drawings

CARDANOL-BASED REACTIVE DILUENTS AND THEIR USE AND PREPARATION

This application is a national stage application under 35 U.S.C. § 371 of PCT/EP2022/054801, filed Feb. 25, 2022, which claims the benefit of European Application No. 21159740.6, filed Feb. 26, 2021, each of which is incorporated herein by reference.

TECHNICAL FIELD

The present invention relates to certain cardanol-derived compounds and mixtures of such compounds suitable for use as reactive diluents in UV-curable compositions, the UV-curable compositions including such compounds and/or mixtures, and methods of preparing the same.

CROSS REFERENCE TO RELATED APPLICATIONS

None

BACKGROUND

Reactive diluents are used in a wide variety of UV-curing systems for applications including but not limited to a variety of coatings, paints, adhesives, and 3D printing. In addition to reducing the viscosity of the composition or resin with which such diluents are associated, they should be reactive in the sense that they contribute to polymerization and/or cross-linking reactions that occur after their associated composition or resin is subjected to actinic radiation of a sufficient wavelength and intensity. Furthermore, depending on the intended end-use application, such diluents must be fast-curing and be able to impart or contribute to the formation of desired physical properties in the object or coating cured therefrom. Yet other selection criteria include volatility and compatibility in the accompanying composition or resin. Of course, it is desired that such diluents are capable of being produced in a cost-effective manner on an industrial scale as well.

Reactive diluents based upon a number of different chemical genera exist, including those based on styrenes, epoxides, and acrylics, to name a few. Acrylic-based reactive diluents, such as acrylates or methacrylates, are useful in a plethora of applications given their versatility in creating objects with a wide range of physical properties. Such acrylates and methacrylates are also typically highly reactive, and are known to form cured products having the desired end-state properties in a relatively short period of time. For that reason, they are used in UV-curing applications where rapid network build-up is of paramount importance, such as in 3D printing applications or processes for coating optical fibers. Acrylates are described in, *Acrylate Polymers for Advanced Applications*, edited by Angel Serrano-Aroca, Published: May 6th 2020, ISBN: 978-1-78985-184-7 (and in particular, the chapter titled "Properties and Applications of Acrylates" by Kingsley Kema Ajekwene).

Although versatile and fast-curing, most commonly-used industrial (meth)acrylate reactive diluents, such as those based on certain alkylphenols, are petroleum-based. In addition to the environmental concerns associated with the manufacture and use of such products, some of them also possess cytotoxicity profiles which make them undesirable for several end-use applications.

Thus, there exists a desire in various industries to fashion UV-curable products utilizing raw materials from more sustainable sources. The recent and growing trend is to source more sustainable alternatives to such petroleum-based products, such as via the provision of bio-based raw materials. Some widely used reactive diluents already exist which can be synthesized from bio-based sources. An example of this includes those made from isoborneol, which itself is a derivative of camphor, an oil found in certain coniferous trees.

It should be noted, however, that many commercially prevalent bio-based materials are also not optimal from a cytotoxicity standpoint, and therefore do not necessarily offer an improved safety profile over their petroleum-based analogues. Thus, materials from other bio-based sources are desired.

Cardanol, a phenolic lipid which is derivable from the anacardic acid found in cashew nuts and shells, offers particular potential as a bio-based, non-toxic raw material in fashioning various industrial chemicals. Historically, cardanol has been utilized as a raw material to create friction particles, surfactants, dispersants, emulsifiers, and phenalkamine curing agents. Despite this, currently only a fraction of the cardanol obtained as a result of cashew nut processing has found any industrial application, resulting in an unused surplus.

Certain cardanol-based (meth)acrylate compounds are known. KR20100133681A describes certain non-ethoxylated, cardanol-derived (meth)acrylate products having a mixture of phenol derivatives with four different kinds of alkyl groups in the meta position. Such phenol derivatives include 1-5% of fully hydrogenated variants. The preparation of such products is also described, along with polymers derived therefrom, which purport to possess use in the industrial fields of coatings, adhesives, plastics, composites, or nanomaterials.

CN107089914A describes preparation methods to produce non-ethoxylated cardanol-based reactive diluents for use in UV-curing systems. In such methods, the anacardic acid from cashew nut shell liquid is esterified in the presence of a catalyst, acid binding agent, polymerization inhibitor, and organic solvent, whereupon it is further purified and cleaned.

CN110483300A describes certain acrylic acid anacardiol polyoxyethylene esters having fully hydrogenated alkyl tails and a high degree (10) of ethoxylation. Such compounds are stated to be useful as a demulsifier to improve crude extraction in heavy oil mining operations.

GB828496A describes acrylic esters of alcohol ethers of phenols having aliphatic hydrocarbon substituents of 8-28 carbon atoms on their phenolic, aromatic nuclei and (co) polymers derived therefrom. Such compounds are stated to be useful as plasticizers for rubbery materials or in combination with epoxy resins to provide cured products which are softer, more pliable and more flexible than the products obtained in the absence of such compounds. Acrylic esters of alcohol ethers of phenols having a pentadecyl group attached in the 3-position with respect to the phenolic oxygen atom and having an ethoxylation degree of 1 or 2 or a propoxylation degree of 1 are exemplified.

U.S. Pat. Nos. 3,046,226A and 3,214,406A describes acrylic esters of alcohol ethers of phenols having aliphatic hydrocarbon substituents of 8-18 carbon atoms on their phenolic, aromatic nuclei and copolymers derived therefrom. Such copolymers are stated to be useful as lubricating oil additives. Acrylic esters of alcohol ethers of phenols having a nonyl or dodecyl group attached in the 3-position with respect to the phenolic oxygen atom and having an ethoxylation degree of 1 and acrylic esters of alcohol ethers of phenols having a pentadecyl group attached in the 3-position with respect to the phenolic oxygen atom and having an ethoxylation degree of 1 or 2 or a propoxylation degree of 1 are described.

None of the aforementioned references, however, describe cardanol-derived (meth)acrylate compounds which are sufficiently suitable for use as reactive diluents in many UV-curing applications. This is due to a variety of reasons, including but not limited to the fact that such materials would not act as a suitable diluent (i.e. reducing the viscosity of the composition or resin with which such diluents are associated), are not capable of providing desired ultimate modulus values, are not sufficiently fast-curing (or are even not tailored for UV-cure at all), and/or are not able to impart a rapid modulus buildup into the cured product(s) created therefrom given the processing conditions of several known industrial applications.

Thus, there exists a heretofore unmet need for the provision of reactive diluents suitable for use in UV-curing systems and/or compositions which simultaneously offer comparable or superior performance to existing industrial reactive diluents, and yet are derived from more sustainable sources and/or improve upon some of the safety, health, and/or environmental concerns associated therewith.

Additionally or alternatively, there is a heretofore unmet need to provide reactive diluents, preferably novel cardanol-derived reactive diluents, along with a preparation method thereof, that is suitable for use in UV-curing applications, and which can improve upon one or more of the drawbacks of existing cardanol-derived compounds as described above.

BRIEF SUMMARY

Described herein are several aspects and embodiments of the invention. A first aspect is a compound of the following formula (Ia):

(Ia)

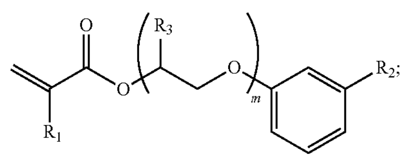

wherein

- $R_1$ is H or $CH_3$;
- $R_2$ is a $C_Y$ alkyl chain having a number of H atoms defined by the expression X(2Y+1); wherein Y is from 9 to 15 and X is from 0.93 to 1.0;
- $R_3$ is H or a $C_1$-$C_4$ alkyl chain, more preferably H or $CH_3$; and
- m is at least 3, preferably at least 4 and m is at most 9, preferably at most 8, more preferably at most 7, even more preferably at most 6, even more preferably at most 5. Most preferably m is 4 or 5.

It has surprisingly been found that the compounds according to the invention are capable to act as a suitable diluent (i.e. reducing the viscosity of the composition or resin with which such diluents are associated), are capable to give sufficiently fast-curing, are capable of providing desired ultimate modulus values, and/or are able to impart a rapid modulus buildup into the cured product(s) created therefrom. An additional advantage is that the viscosity-reducing effect of compounds according to the invention is less sensitive to temperature fluctuations compared to ethoxylated (EO)4 nonyl phenol acrylate.

According to other embodiments of the first aspect, the compound is a cardanol derived monomer and may be used as a diluent in various compositions, preferably UV-curable compositions. The compound possesses a high-degree of hydrogenation; in preferred embodiments the alkyl chain $R_2$ of the compound is fully hydrogenated. In yet further embodiments, the compound is defined by other expressions or ranges for one or more of the substituents listed in formula (Ia). Compounds according to other embodiments of the first aspect possess specified number average molecular mass values, such as between 400 to 800 grams per mole.

A second aspect of the current invention is a composition or mixture comprising, consisting of, or consisting essentially of one or more of the compounds described according to any of the embodiments of the first aspect. In various specific embodiments of the second aspect, the composition or mixture comprises certain quantities of biobased content, such as higher than 20 wt. %, or from 20-80 wt. %. In yet further embodiments of the second aspect, the compositions or mixtures contain specified purity values, whereas purity is defined with respect to various compounds or groups of compounds according to various embodiments of the first aspect of the invention. According to various embodiments, said purity values may be, e.g., at least 80%, or at least 90%. These purity values may be taken with respect to more specific iterations of compounds of formula (Ia) according to the first aspect, such as with respect to fully hydrogenated versions thereof.

A third aspect of the invention is a UV-curable composition comprising one or more of the compounds described according to any of the embodiments of the first aspect and/or any of the compositions or mixtures according to any of the embodiments of the second aspect of the invention. In an embodiment of the third aspect, the UV-curable composition contains various amounts of the compounds according to the first aspect and/or the compositions or mixture according to the second aspect. In various embodiments of the third aspect, the UV-curable composition comprises a first diluent monomer component, wherein the first diluent monomer component consists of: (i) compounds according to any of the embodiments of the first aspect, and/or (2) compositions or mixtures according to any of the embodiments of the second aspect. In yet further embodiments of the third aspect, the UV-curable composition possesses prescribed cure performance values, such as a $T_{30\%,\ modulus\ max}$ of less than 1 second, per a method described herein.

A fourth aspect of the invention is a method of preparing a compound according to any of the embodiments of the first aspect and/or a composition or mixture according to any of the embodiments of the second aspect of the invention, the method comprising the steps of (a) providing a cardanol, such as a cardanol derived from a cashew nut shell liquid, wherein the cardanol comprises a phenol group and an alkyl chain; (b) alkoxylating the phenol group of the cardanol; (c) subjecting the cardanol to a hydrogenation step, such that the alkyl chain is at least 93%, preferably at least 99% hydrogenated; and (d) esterifying the cardanol with a (meth) acrylic acid to functionalize it with a single (meth)acrylate group; wherein steps (b) and (c) are interchangeable.

BRIEF DESCRIPTION OF THE DRAWINGS

None

DETAILED DESCRIPTION

A first aspect of the current invention is a compound of the following formula (Ia):

(Ia)

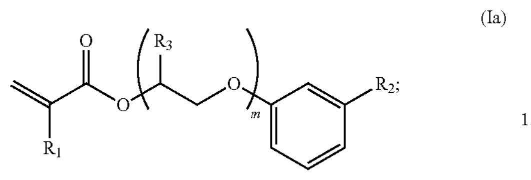

wherein

- $R_1$ is H or $CH_3$;
- $R_2$ is a $C_Y$ alkyl chain having a number of H atoms defined by the expression X(2Y+1); wherein Y is from 9 to 15 and X is from 0.93 to 1.0;
- $R_3$ is H or a $C_1$-$C_4$ alkyl chain, or H or $CH_3$; and
- m is at least 3, preferably at least 4 and m is at most 9, preferably at most 8, more preferably at most 7, even more preferably at most 6, even more preferably at most 5. Most preferably m is 4 or 5.

In a preferred embodiment, the compound according to formula (Ia) is derived from cardanol. Cardanol is a bio-based mixture of phenolic lipids which of decarboxylated derivatives obtained from the thermal decomposition of any anacardic acid, a substance which naturally occurs in the shells of nuts (hereinafter referred to as "cashew nut shell oil" or "CNSL") from the cashew tree *Anacardium occidentale*. Cardanol is readily produced as a non-edible byproduct of cashew nut processing for food use. Global annual production of cardanol is believed to approach 1 metric ton annually, although industrial demand has not yet met this supply.

The general chemical structure for cardanol is represented by the following formula (I):

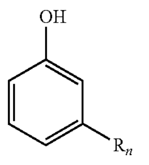

wherein, in cardanols produced via the processing of CNSL, $R_n$ is a $C_{15}$ alkyl chain comprising a mixture of each of the following four substituents $R_1$-$R_4$:

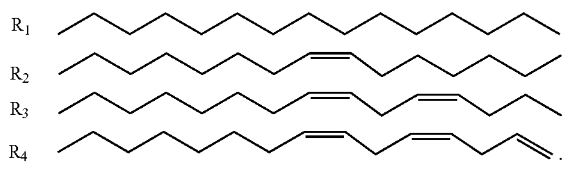

Cardanol produced by the thermally-driven decarboxylation of anacardic acid includes more than one compound because the identity of the pendant alkyl chain varies in its degree of unsaturation. The predominant compound is $R_4$, a tri-unsaturated cardanol, which typically accounts for approximately 41 wt. % of the total. The remaining cardanol species by order of descending quantity include the mono-unsaturated species $R_2$ (approximately 34 wt. %), followed by the bi-unsaturated $R_3$ (approximately 22 wt. %), and finally the saturated $R_1$ (approximately 2 wt. %).

In a preferred embodiment, therefore, the compound of formula (Ia) is derived from cardanol; that is, it utilizes one or more of the cardanol species described in formula (I) above as a raw material in its synthesis. In an embodiment, such a cardanol-derived monomer is obtained from CNSL.

According to other embodiments, a number of specific variants according to formula (Ia) may be utilized, either alone or in combination. In embodiments of the first aspect, substituent $R_2$ from formula (Ia) is a $C_Y$ alkyl chain having a number of H atoms defined by the expression X(2Y+1); wherein Y is from 9 to 15 and X is from 0.93 to 1.0. Where cardanol is used as the starting raw material, Y is equal to 15, although of course naturally-occurring variants may exist in any starting raw material. The number of hydrogen atoms in this alkyl chain may vary as a function of the number of its carbon atoms. Where Y itself is 15, according to the expression defined above, the alkyl chain may include varying quantities of hydrogen atoms. When it is fully saturated, it will possess 31H atoms; this occurs wherein X=1.0. This arrangement defines the alkyl chain $R_1$ from formula (I) depicted above. The alkyl chain will possess only 25 hydrogen atoms, meanwhile, when X approaches 0.8. This arrangement defines the alkyl chain $R_4$ from formula (I) depicted above. Of course other variants may be readily contemplated by the person having ordinary skill in the art to which this invention applies.

The compound according to formula (Ia) possesses a high degree of saturation such that X is at least 0.93. In another embodiment, X is greater than 0.93. In still a further embodiment, X is greater than 0.99. In a preferred embodiment, the compound according to formula (Ia) is fully saturated and $R_2$ from formula (Ia) possesses a $C_{15}H_{31}$ structure per the alkyl chain of $R_1$ from formula (I).

Hydrogenation is a useful means for converting unsaturated compounds into saturated derivatives. In various embodiments, therefore, the raw material from which the compound of formula (Ia) is derived, such as a cardanol per formula (I) above, is subjected to a hydrogenation process to increase its degree of saturation. Hydrogenation is a chemical reaction between molecular hydrogen ($H_2$) and another unsaturated compound called a substrate, in order to yield a product having a reduction in the number of double and triple bonds which were present originally in the substrate. Typically, the substrate is an organic compound, such as a hydrocarbon compound. Hydrogenation typically constitutes the addition of pairs of hydrogen atoms to the substrate molecule, such as an alkene. Hydrogenation reactions are known and are described in, i.a., *Advanced Organic Chemistry,* 7th ed. (2014), such as at chapter 15-11, p 902-909; and *Comprehensive Organic Synthesis II*, such as at chapter 8.16, pp. 564-600.

Although some hydrogenation reactions are possible in the absence of a catalyst, such reactions must be carried out at extremely high temperatures and are industrially impractical. Furthermore, $H_2$ is unreactive with most organic compounds in the absence of metal catalysts. A variety of metal catalysts, such as nickel, palladium, or platinum, is typically used in the hydrogenation of organic compounds. The use of nickel is common despite its relative low degree of activity, primarily due to its low cost compared to other precious metals.

Catalysts may be classified at a high level as either homogeneous catalysts or heterogeneous catalysts. Homogeneous catalysts dissolve in the solvent that contains the unsaturated substrate. Commonly utilized homogeneous catalysts activate both the unsaturated substrate and the $H_2$. Many homogeneous catalysts are based on platinum-group metals, such as Rh and Ir. Specific non-limiting examples include dichlorotris(triphenylphosphine)ruthenium(II), Crabtree's catalyst, $Rh_2Cl_2(cod)_2$, and (S)-iPr-PHOX.

Heterogeneous catalysts, on the other hand, are solids that are suspended in the same solvent with the substrate or are treated with gaseous substrate. They are typically more common in industrial hydrogenation processes. In industry, precious metal hydrogenation catalysts are deposited from solution as a fine powder on the support, which is a cheap, bulky, porous, usually granular material, such as activated carbon, alumina, calcium carbonate or barium sulfate. For example, platinum on carbon is produced by the reduction of chloroplatinic acid in-situ in carbon. Certain non-limiting examples of these catalysts include 5% ruthenium on activated carbon, or 1% platinum on alumina. Base metal catalysts, such as Raney nickel, may also be used.

Hydrogenation reactions may be carried out via a number of different processes. Three classes of such processes include batch hydrogenation under atmospheric conditions, batch hydrogenation at elevated temperatures and/or pressures, and flow hydrogenation. The means for preparing an inert reaction environment, the means for supplying hydrogen, the pressures and/or temperatures under which the reactants are supplied and/or the reaction is carried out, the treatment of the substrate-hydrogen-catalyst mixture, and the means for extracting the resulting product, among other factors, may vary as will be appreciated by the skilled artisan, depending upon, e.g., the specific nature of the substrate and catalyst used, the desired reaction output, energy input, reaction efficacy, and cost.

In an embodiment, therefore, the compound according to formula (Ia) has been subjected to a hydrogenation reaction. In a preferred embodiment, the compound according to formula (Ia) is fully hydrogenated, or as used herein, its alkyl chain in substituent $R_2$ possesses no double or triple bonds. Inventors have observed that the presence of such unsaturation negatively impacts the ability of cardanol-derived reactive diluents to engage in sufficient cure under UV conditions.

Compounds according to formula (Ia) of the first aspect of the invention are further modified from cardanol itself in the sense that the phenol of the raw material is disrupted. That is, compounds according to formula (Ia) of the first aspect of the present invention involve a reaction such that the aromatic ring of cardanol is no longer bonded to an alcohol group.

The foregoing disruption may be carried out by a number of different means, although in a preferred embodiment, the cardanol is subjected to an alkoxylation process. Alkoxylation is a chemical reaction in which an active hydrogen compound, such as an alcohol, phenol, or amine, is reacted with an cyclic ether for example an epoxide or oxetane. A typical manifestation of this reaction is the ethoxylation of alcohols (ROH), in which case ethylene oxide is the alkoxylating agent per the following reaction scheme, known as ethoxylation:

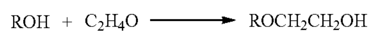

Another industrially significant epoxide is propylene oxide ($OCH_2CHCH_3$). Propylene oxide is typically used for alkoxylation to produce polyether polyols. This alkoxylation process is shown in simplified form below in a reaction scheme known as propoxylation:

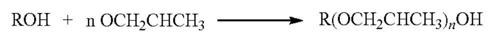

Notably, either ethoxylation or propoxylation may be performed multiple times by reacting additional epoxides as desired, often for the purpose of increasing the alkoxylated chain length. If the reaction is carried out multiple times, it may be referred to as polyethoxylation or polypropoxylation. Control of the chain length depends on the catalyst selected and the conditions under which the reaction is made to occur.

Alkoxylation reactions are known to be highly exothermic and require efficient heat exchange to maintain the safety and control of the reaction. A variety of catalysts may be used to accompany alkoxylation reactions, although certain alkaline catalysts, such as sodium hydroxide or potassium hydroxide, are most commonly used.

Compounds of formula (Ia) of the first aspect of the present invention may be propoxylated, ethoxylated, or both. The resulting lengthened chain may be represented by a variety of different chemical structures, depending on the nature of the alkoxylation reaction utilized. The substituent $R_3$ of this chain is either H or a $C_1$-$C_4$ alkyl chain. In a preferred embodiment, $R_3$ is represented either by H or $CH_3$.

The value for substituent m is linked to the number of alkoxylation reactions to which the raw material, preferably the cardanol or cardanol that has been subjected to a hydrogenation step, has been subjected. As referred to herein, this number of alkoxylation reactions is referred to as the degree of alkoxylation. m is at least 3, preferably at least 4 and m is at most 9, preferably at most 8, more preferably at most 7, even more preferably at most 6, even more preferably at most 5. In embodiments of the first aspect of the invention, the compound has been subjected to a range spanning three degree of alkoxylation (m=3), to nine degrees of alkoxylation (m=9). In other embodiments, m is selected from any value from 3 to 8, or from 3 to 7, or from 3 to 6, or from 3 to 5. In other embodiments, m is selected from any value from 4 to 9, or from 4 to 8, or from 4 to 7, or from 4 to 6. In an embodiment, the compound according to formula (Ia) has been subjected to four or five degrees of ethoxylation or propoxylation, such that m=4 or 5.

Inventors have presently and surprisingly discovered that certain alkoxylated versions of cardanol-derived reactive diluents with a degree of alkoxylation from 3 to 9, or from 3 to 8, or from 3 to 7, or from 3 to 6, or from 3 to 5, or from 4 to 9, or from 4 to 8, or from 4 to 7, or from 4 to 6, or of 4 or 5 are preferable to their analogues with one degree of alkoxylation, as they are observed to, i.a., exhibit a faster modulus build-up under UV-curing conditions. Therefore, Inventors have surprisingly discovered that compounds otherwise according to formula (Ia) with a different degree of alkoxylation may not be sufficiently tailored for use in industrial UV-curing applications requiring a quick modulus build-up, such as those in fiber optic coating processes or certain 3D printing applications.

The foregoing observation is particularly unexpected, because it would have been presumed ex ante that said analogues with one degree of alkoxylation of compounds according to formula (Ia) of the first aspect of the current invention would be preferable both as a reactive compound and as a diluent. This would have been expected because, given their relatively lower molecular mass and concomitantly higher double bond concentration, said variants with one degree of alkoxylation would be expected to react more quickly.

Regardless of the foregoing, Inventors have discovered that beyond a certain point, the detriments associated with too many degrees of alkoxylation outweigh the surprising benefits in facilitating effective reactive diluents for UV-curing applications. Thus, if the degree of alkoxylation becomes too large, that is 10 or above, the viscosity of the resulting compound becomes too high such that it no longer is suitable for use as a diluent in most UV-curable compositions. As used herein, a diluent is a substance which reduces the viscosity of the greater composition into which it is added or with which it is associated. Therefore, compounds according to formula (Ia) will possess fewer than 10 degrees of alkoxylation.

Furthermore, in order to ensure suitability for use as a diluent, compounds according to formula (Ia) may possesses specified molecular mass values. In various embodiments, the number average molecular mass of compounds according to formula (Ia), when measured by a suitable method such as a size exclusion chromatography (SEC) method, is from 400 g/mol to 800 g/mol, or from 400 g/mol to 770 g/mol, or from 400 g/mol to 750 g/mol, or from 450 g/mol to 750 g/mol, or from 500 g/mol to 750 g/mol.

In addition to the foregoing, in order to be useful as a reactive diluent, the compound of formula (Ia) must be tailored so that it possesses a suitable reactive group. As used herein, "reactive" means the ability to form a chemical reaction, preferably a polymerization reaction, with another molecule. As such, a reactive compound will be said to possess at least one reactive, or functional group. Although a variety of functional groups can be envisioned, it is preferred that such reactive or functional group is a polymerizable group. It is further preferred that such group is reactive in response to UV-curing and as part of a UV-curable composition.

Such a reactive group does not occur naturally in, e.g., cardanol itself, so the raw material would need to be further modified to incorporate a reactive group. Although a variety of reactive groups can be envisioned, in embodiments of the first aspect, this reactive group may be an acrylate group or a methacrylate group. A contemplation of using either group, referred to herein using the common shorthand (meth) acrylate, is preferred given such compounds' known high degrees of double-bond reactivity and ability to impart final-state properties in a relatively quick timeframe under UV-curing conditions, as opposed to other reactive groups that rely on ring-opening cationic polymerization reactions, such as epoxides or oxetanes. (Meth)acrylates also exhibit characteristic pH-dependent water solubility, and they are readily capable of forming polymers that are rubbery, soft, tough, have a good impact resistance, transparency, elasticity, and reasonable ozone, heat and oil resistance, and good weatherability.

The (meth)acrylate functional group is preferably added to, e.g., the cardanol via an esterification reaction. Esterification is the process of combining an organic acid (RCOOH) with an alcohol (ROH), preferably in the presence of a suitable catalyst to form an ester (RCOOR) and water. Ester is obtained by an esterification reaction of an alcohol and a carboxylic acid. In preferable esterification reactions utilized to fashion compounds according to formula (Ia) of the first aspect, an organic acid is reacted with a hydroxyl group on the, e.g., alkoxylated and/or hydrogenated cardanol to form an acrylate group or methacrylate group.

Catalysts are preferably used to facilitate the esterification reaction. Many suitable esterification catalysts are known, including the TREVER®|LYST series of catalysts from Chemra, including TREVER®|LYST CAT160, CAT200, TREVER®|LYST CAT360, CAT390, CAT410, and XS102, to name a few non-limiting examples.

In order to fashion an acrylate functional group to a compound of formula (Ia), preferably acrylic acid may be reacted therewith. If, on the other hand, a methacrylate functional group is desired, the addition of methacrylic acid may be used, although of course other possibilities exist. The quantities of reactants, the reaction conditions, suitable equipment, and means for extracting the reacted product, among other relevant factors, may be specified as desired as will be appreciated by the skilled artisan to which this invention applies.

Accordingly, compounds according to formula (Ia) possess an $R_1$ substituent that is either a hydrogen atom or $CH_3$. If the esterification reaction results in the addition of an acrylate group, then $R_1$ would be H; if, on the other hand, the esterification reaction results in the addition of a methacrylate group, then $R_1$ would be $CH_3$. Between the two, acrylate groups are preferred for many UV-curing applications where cure speed is paramount.

Compounds according to the first aspect of the invention may be used in a variety of applications. Such compounds may be incorporated into biocompatible compositions useful in dentistry and many other biomedical applications, and cosmetics such as eyeliner, liquid makeups, mascaras, nail polish, sunscreens, lipsticks, and skin care products.

Alternatively, such compounds may be used in the manufacture of superabsorbent products such as diapers, as well as floor polishes, paints, coatings and adhesives of various types.

They also find major applications in coatings and paints such as solvent-born coatings, emulsion paints, interior and exterior water-based paints, and printing inks for applications that need quick drying rates such as auto based lacquers and industrial coatings. They are also potentially useful in pressure sensitive adhesive formulations, including those having low adhesion to those which are intended to bond permanently to substrates, textiles, automotive products, leather finishing, tape adhesives, high-temperature-resistant and oil-resistant elastomers.

It is preferable that such compounds are used in applications wherein the associated composition is UV-curable and intended to be subjected to exposure of actinic radiation of a prescribed wavelength and intensity. Particular non-limiting examples of these applications include coating of optical fibers, as well as various additive manufacturing applications such as stereolithography or digital light processing (DLP).

A second aspect of the current invention is a composition or mixture comprising, consisting of, or consisting essentially of one or more of the compounds described according to any of the embodiments of the first aspect. As contemplated herein, a composition according to the second aspect may include any number of distinct chemical components, including a single chemical component. A mixture, on the other hand, will be understood to include at least two distinct chemical components.

Indeed, it is understood that in a real-world laboratory or commercial attempt to create any specific compound according to formula (Ia) as described elsewhere herein, multiple chemical species will invariably be created. The level of purity or spread and quantity of different chemical products in any reaction will necessarily vary, depending upon a multitude of factors, including but not necessarily limited to the precision of the stoichiometric calculations, measuring apparatuses used, and the quality and cleanliness of the reaction vessels and related equipment. Thus, it is understood that attempts to carry out reactions yielding only a specific single chemical compound according to any of the embodiments of the first aspect of the invention will not be completely successful. In an embodiment of the second aspect, therefore, the composition or mixture comprises, consists of, or consists essentially of compounds according to formula (Ia). In another embodiment, the composition or mixture comprises, consists of, or consists essentially of any compound according to any of the embodiments of the first aspect of the invention. In certain embodiments, the composition or mixture itself will be construed to mean all chemical species present which were the product of the same reaction leading to any of the compounds according to formula (Ia). When such a meaning is ascribed, the composition or mixture according to the second aspect may be used or considered as a single raw material or component for use in a composition including other chemical components, such as the UV-curable compositions described in embodiments of the third aspect of the invention described elsewhere herein, infra.

In a preferred embodiment, the composition or mixture has a high purity of fully-hydrogenated variants according to formula (Ia). Therefore, in an embodiment, the composition or mixture possesses a purity of at least 90%, or at least 95%, or at least 98%, or at least 99%, or from 90-99.9%; wherein purity is defined as a percentage by weight of a compound according to formula (Ia) wherein Y=15 and X=1.0, relative to the weight of the entire composition or mixture, as measured by a suitable method such as a size exclusion chromatography (SEC) method. In an embodiment, the aforementioned composition or mixture is to be construed as all compounds which were the product of the same reaction or reactions leading to the compounds according to formula (Ia).

As mentioned, the compounds according to various embodiments of the first aspect of the invention are derived preferably from bio-based sources such as cardanol. Accordingly, in certain embodiments of the second aspect of the invention, the composition or mixture comprises a certain degree of biobased content. In an embodiment, the composition or mixture comprises at least 20 wt. %, or at least 30 wt. %, or at least 40 wt. %, or at least 50 wt. %, or from 20-80 wt. %, or from 20-70 wt %, or from 20-60 wt. %, or from 20-50 wt. %, or from 30-80 wt. %, or from 30-60 wt. %, or from 40-80 wt. %, or from 40-60 wt. % of biobased content. In an embodiment, the composition or mixture itself may include only the chemical products of a reaction or reactions which yielded any of the compound(s) according to formula (Ia). Biobased content may be determined by any suitable means, although a determination in accordance with ISO 16620-2:2019 is considered a particularly preferred method for doing so.

Of course, biobased content will necessarily vary depending upon the desired structure of the compound according to formula (Ia). Compounds with a high degree of ethoxylation, for example, will necessarily incorporate a relatively smaller percentage of the residue of cardanol in the final compound. However, if cardanol is used exclusively as a starting reactant, a desirable quantity of biobased content will remain in the final product.

In a further embodiment of the second aspect, the composition or mixture will be water-free or substantially water-free. In a preferred embodiment, the composition or mixture will be solvent-free or substantially solvent-free. In an embodiment, therefore, the composition or mixture possesses less than 1 wt. % of solvent and/or less than 1 wt. % of water, or less than 0.5 wt. % of solvent and/or less than 0.5 wt. % of water, or less than 0.1 wt. % of solvent and/or less than 0.1 wt. % of water, wherein the solvent or water content of the composition or mixture may be determined according to any suitable method.

A third aspect of the invention is a UV-curable composition comprising one or more of the compounds described according to any of the embodiments of the first aspect and/or any of the compositions or mixtures according to any of the embodiments of the second aspect of the invention. As mentioned, compounds according to formula (Ia) as discussed elsewhere herein are suitable for use as reactive diluents for use in UV-curable compositions. Accordingly, in an embodiment of the third aspect, the UV-curable composition contains one or more reactive diluent monomer components, wherein a first diluent monomer component consists of, or consists essentially of, compounds according to any of the embodiments of the first aspect of the invention, and/or compositions or mixtures according to any of the embodiments of the second aspect of the invention.

As used herein, a diluent monomer component comprises a plurality of individual reactive diluent monomer molecules. A diluent monomer component may include a variety of reactive diluent monomer types, although these are generally regarded as impurities, given that it is contemplated herein that all such types are a product of the same chemical reaction. Typically, when formulating a UV-curable composition, a reactive diluent monomer component is supplied as a distinct raw material under a chemical tradename, wherein the raw material itself is marketed commercially as a single chemical compound of a specified type.

In an embodiment, therefore, the UV-curable composition contains at least 0.1 wt. %, or at least 0.5 wt. %, or at least 1 wt. %, or at least 5 wt. %, or at least 10 wt. %, or at least 25 wt. %, or at least 50 wt. %, or from 1 to 70 wt. %, or from 1 to 50 wt. %, or from 1 to 25 wt. %, or from 1 to 10 wt. %, or from 1 to 5 wt. %, or from 5 to 65 wt. %, or from 5 to 50 wt. %, or from 5 to 15 wt. %, or from 10 to 70 wt. %, or from 10 to 50 wt. % of a first diluent monomer component, relative to the weight of the entire composition, wherein the first diluent monomer component consists of or consists essentially of compounds according to formula (Ia):

(Ia)

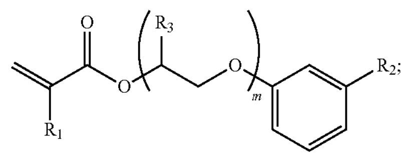

wherein $R_1$ is H or $CH_3$;

$R_2$ is a $C_Y$ alkyl chain having a number of H atoms defined by the expression X(2Y+1); wherein Y is from 9 to 15 and X is from 0.93 to 1.0;

$R_3$ is H or a $C_1$-$C_4$ alkyl chain, more preferably H or $CH_3$; and m is at least 3, preferably at least 4 and m is at most 9, preferably at most 8, more preferably at most 7, even more preferably at most 6, even more preferably at most 5. Most preferably m is 4 or 5.

In an embodiment, the first reactive diluent monomer component comprises, consists of, or consists essentially of fully hydrogenated compounds according to formula (Ia), such as those wherein Y=15 and X=1.0. In an embodiment, therefore, the UV-curable composition comprises a first diluent monomer component, wherein the first diluent monomer component possesses a purity of least 90%, or at least 95%, or at least 98%, or at least 99%, or from 90-99.9%; wherein purity is defined as a percentage by weight of a compound according to formula (Ia) wherein Y=15 and X=1.0, relative to the weight of the entire first reactive diluent monomer component, as measured by a suitable method such as a size exclusion chromatography (SEC) method.

In addition to a first diluent monomer component, the UV-curable compositions according to the third aspect include other components, such as (photo)initiators, reactive oligomers, and even additional diluent monomer components.

Although waterborne or aqueous UV-curable compositions are known and are not expressly excluded herein in all instances, in a preferred embodiment, the UV-curable composition according to the third aspect will be water-free or substantially water-free. In a preferred embodiment, the UV-curable composition will be solvent-free or substantially solvent-free. In an embodiment, therefore, the UV-curable composition possesses less than 1 wt. % of solvent and/or less than 1 wt. % of water, or less than 0.5 wt. % of solvent and/or less than 0.5 wt. % of water, or less than 0.1 wt. % of solvent and/or less than 0.1 wt. % of water, wherein the solvent or water content of the UV-curable composition may be determined according to any suitable method. Water content, for example, is preferably determined via the Karl Fischer titration method, which is described in a variety of sources, including the guide titled Good Titration Practice™ in Karl Fischer Titration by Mettler Toledo. Other solvents, such as propylene carbonate, may be readily identified and quantified via SEC methods.

In an embodiment, the UV-curable composition according to the third aspect of the present invention further comprises a. one or more oligomers having one or more ethylenically unsaturated groups, preferably having one or more (meth)acryoyl or vinyl groups, and b. a photoinitiator, c. optionally, one or more additives.

Preferably, the one or more oligomers having one or more ethylenically unsaturated groups are independently selected from urethane (meth)acrylate oligomers, polyester (meth) acrylate oligomers and epoxy (meth)acrylate oligomers, more preferably the one or more oligomers having one or more ethylenically unsaturated groups are urethane (meth) acrylate oligomers. Even more preferably, the one or more oligomers having one or more ethylenically unsaturated groups are di- or trifunctional telechelic urethane (meth) acrylate oligomers with at least 4 urethane groups and a number average molecular weight (Mn) from 750-100000 g/mol or at least 1000 g/mol, or at least 1250 g/mol, or at least 1500 g/mol, or an Mn of less than 60,000 g/mol, or less than 40,000 g/mol, or less than 30,000 g/mol, or between 1000 to 20,000 g/mol, or between 1500 to 15,000 g/mol. Preferably, the urethane (meth)acrylate oligomers is the reaction product of at least the following reactants:

(i) a hydroxy-functional backbone compound, (ii) an isocyanate compound; and (iii) a hydroxyl-functional end-capper further comprising a (meth)acrylate functional group;

wherein a molar ratio of the number of isocyanate groups in (ii) to the number of hydroxyl-groups in (i) in the urethane (meth)acrylate oligomer (b) is greater than 1.0, more preferably from about 1.5 to about 2.0.

The hydroxyl-functional backbone compound (i) preferably comprises a polyether, polyester, polybutadiene, polycarbonate, or silicone moiety. More preferably, the hydroxyl-functional backbone compound (i) comprises, consists essentially of, or consists of a polyether moiety, more preferably a polypropylene glycol moiety or a polytetrahydrofuran moiety.

The isocyanate compound (ii) preferably comprises, consists essentially of, or consists of isophorone diisocyanate, 2,4-isomer toluene diisocyanate, 4,4'-methylenedicyclohexyl diisocyanate, 1,5-pentane diisocyanate, 2,2,4-trimethyl-hexamethylene diisocyanate, 2,4,4-trimethyl-hexamethylene diisocyanate, or hexamethylene diisocyanate, or combinations thereof.

Suitable examples of the hydroxyl-functional end-capper further comprising a (meth)acrylate functional group (compound (iii)) include (meth)acrylates derived from (meth) acrylic acid and epoxy and (meth)acrylates comprising alkylene oxides, more in particular, 2-hydroxy ethyl (meth) acrylate, 2-hydroxypropyl(meth)acrylate, 2-hydroxy-3-phenoxypropyl(meth)acrylate, and hydroxyethyl caprolactone acrylate, ethoxylated trimethylolpropane diacrylate, glycerol di(meth)acrylate, and glycerol acrylate methacrylate (i.e., 3-(Acryloyloxy)-2-hydroxypropyl methacrylate). In a preferred embodiment, (iii) comprises, consists essentially of, or consists of hydroxyethyl (meth)acrylate, 2-hydroxypropyl (meth)acrylate, 3-hydroxypropyl (meth)acrylate, 4-hydroxybutyl (meth)acrylate, caprolactone (meth)acrylate, glycerol acrylate methacrylate, glycerol di(meth)acrylate, or combinations thereof.

The one or more oligomers having one or more ethylenically unsaturated groups are preferably present in the UV-curable composition in an amount of at least 45 wt. %, or at least 50 wt. %, or at least 55 wt. %, or at least 60 wt. %, or at least 65 wt. %, or at least 70 wt. %, or at least 80 wt. %, or at least 90 wt. %, or at least 95 wt. %, or at least 98 wt. %, relative to the weight of the entire composition.

In a preferred embodiment of the third aspect of the present invention, the one or more oligomers having one or more ethylenically unsaturated groups are present in the UV-curable composition in an amount of from 50 wt. % to 70 wt. % and the compounds according to any of claims 1-7 are present in the UV-curable composition in an amount of from 25 wt. % to 45 wt. %, relative to the weight of the entire composition.

The photoinitiator (b) is preferably present in the UV-curable composition in an amount from 0.04 wt. % to 8 wt. % and comprises, consists essentially of, or consists of 2,4,6-trimethylbenzoylethoxyphenylphosphine oxide, 2,4,6-trimethylbenzoyldiphenylphosphine oxide, α-hydroxycyclohexyl phenyl ketone, 2-hydroxy-2-methyl-1-phenylpropanone, 2-hydroxy-2-methyl-1-(4-isopropylphenyl) propanone, 2-hydroxy-2-methyl-1-(4-dodecylphenyl) propanone, 2-Hydroxy-1-{4-[4-(2-hydroxy-2-methyl-propionyl)-benzyl]-phenyl}-2-methyl-propan-1-one, or 2-hydroxy-2-methyl-1-[(2-hydroxyethoxy)phenyl]propanone, or combinations thereof.

The UV-curable composition is preferably an optical fiber coating composition.

A fourth aspect of the invention is a method of preparing a compound according to any of the embodiments of the first aspect and/or a composition or mixture according to any of the embodiments of the second aspect of the invention, the method comprising the steps of (a) providing a cardanol, such as a cardanol derived from a cashew nut shell liquid, wherein the cardanol comprises a phenol group and an alkyl chain; (b) alkoxylating the phenol group of the cardanol; (c) subjecting the cardanol to a hydrogenation step, such that the alkyl chain is at least 93%, preferably at least 99% hydrogenated; and (d) esterifying the cardanol with a (meth) acrylic acid to functionalize it with a single (meth)acrylate group; wherein steps (b) and (c) are interchangeable.

According to the methods of preparing a compound according to the fourth aspect, a cardanol raw material is provided as step (a). The cardanol provided is preferably a byproduct of the processing of cashew shell nut liquid. The structure of the provided cardanol follows the general requirements of the following formula (I):

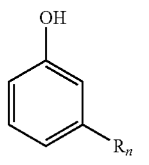

wherein, in cardanols produced via the processing of CNSL, $R_n$ is a $C_{15}$ alkyl chain comprising a mixture of $R_1$-$R_4$ as described elsewhere herein with respect to the first aspect of the invention.

As can be seen, the cardanols of the fourth aspect possess a phenol group and an alkyl chain. In processes according to various embodiments of the fourth aspect, both such groups are further reacted to create the compounds described and claimed elsewhere herein. Accordingly, as step (b), the phenol group of the cardanol is subjected to an alkoxylation reaction.

The alkoxylation reactions, means, catalysts, etc. discussed elsewhere herein with respect to the first aspect of the invention are equally applicable to the present aspect as well. At least with this guidance, the cardanol provided according to the fourth aspect may be subjected to a variety of alkoxylation reactions as will be appreciated by the skilled artisan. In an embodiment, the cardanol is subjected to an ethoxylation reaction or a propoxylation reaction. In a preferred embodiment, the alkoxylation reaction is carried out such that it is responsible for altering the provided cardanol with the structure bound by the repeating parenthesis m per the formula (Ia) below:

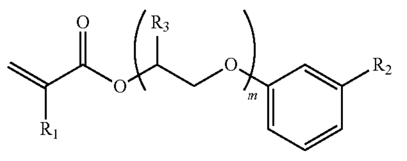

As specified elsewhere herein, the alkoxylation reaction is specified such that a variety of values for $R_3$ and m may be obtained. In a preferred embodiment, the alkoxylation reaction results in $R_3$ being either H or $CH_3$. Finally, the values for m, which reflect the degree of alkoxylation, is in the range from 3 to 9, or from 3 to 8, or from 3 to 7, or from 3 to 6, or from 3 to 5, or from 4 to 8, or from 4 to 9, or from 4 to 8, or from 4 to 7, or from 4 to 6. Most preferably m is 4 or 5. The alkoxylation step described herein may be carried out either before or after the hydrogenation step as desired.

As step (c) of the fourth embodiment, the provided cardanol is also subjected to a hydrogenation reaction. Whereas the alkoxylation is responsible for modification of the phenol group of the provided cardanol, the hydrogenation reaction is carried out with the objective of modifying the alkyl chain (R from formula (I)) thereof. The hydrogenation reactions, means, catalysts, etc. discussed elsewhere herein with respect to the first aspect of the invention are equally applicable to the present aspect as well. At least with this guidance, the cardanol provided according to the fourth aspect may be subjected to a variety of hydrogenation reactions as will be appreciated by the skilled artisan. In a preferred embodiment, the hydrogenation reaction is carried out such that it is responsible for altering the provided cardanol with the structure $R_2$ per formula (Ia) reproduced above.

In a preferred embodiment, the hydrogenation reaction is carried out such that it more fully saturates the alkyl chain $R_2$ of the cardanol. As typical cardanol raw materials will contain roughly only 2 wt. % of fully saturated variants, the hydrogenation reaction will be carried out so as to increase this species to the maximum extent possible. In the present invention, the alkyl chain $R_2$ is at least 93% hydrogenated. In other embodiments, $R_2$ is at least 99% hydrogenated.

As noted above, $R_2$ is a $C_Y$ alkyl chain having a number of H atoms defined by the expression X(2Y+1); wherein Y is from 9 to 15 and X is from 0.93 to 1.0. For the avoidance of doubt, the values for X correspond to the degree of hydrogenation in a particular compound; if X=1, for example, then the alkyl chain will possess the maximum number of hydrogen atoms for a given alkyl chain $C_Y$, regardless of the length Y. Regardless of the foregoing, the provided cardanol may be carried out such that the hydrogenation step (c) occurs either before or after the alkoxylation step (b).

Next, as step (d) of the fourth aspect of the invention, the provided cardanol is subjected to an esterification reaction. This step is employed with the objective of adding a UV-functional group to the cardanol-derived monomer. This is exemplified by the $R_1$-containing structure adjacent to the alkoxylated moiety (or moieties) per formula (Ia) as reproduced above. The esterification reactions, means, catalysts, etc. discussed elsewhere herein with respect to the first aspect of the invention are equally applicable to the present aspect as well. At least with this guidance, the cardanol provided according to the fourth aspect may be subjected to a variety of esterification reactions as will be appreciated by the skilled artisan. In a preferred embodiment, the esterification reaction is carried out such that it is responsible for adding a UV-functional group to the monomer structure. In an embodiment, the UV-functional group is an acrylate group. In another embodiment, the UV-functional group is a methacrylate group.

In embodiments of the fourth aspect, the esterification reaction occurs after both the interchangeable hydrogenation and alkoxylation steps. If the provided cardanol is subjected to an esterification reaction before the hydrogenation and alkoxylation steps, it will not consistently yield a cardanol structure as desired, such as one according to formula (Ia).

The following such examples further illustrate the invention but, of course, should not be construed as in any way limiting its scope.

EXAMPLES

These examples illustrate embodiments of the instant invention. Table 1 describes the various components of the compositions used in the present examples. Tables 2A and 2B and 3 provide test results indicative of the relative performance of various compounds according to the current invention, along with corresponding comparative compounds as relevant.

TABLE 1

Reactants Used

| Component | Chemical Descriptor | CAS and/or Supplier |
|---|---|---|
| Acclaim 8200 (PPG8000) | Bifunctional polypropylene glycol; molecular weight approximately 8000 | Covestro |
| TDI | Toluenediisocyanate; CAS 584-84-9 | Covestro, BASF |
| HEA | 2-hydroxyethyl acrylate; CAS 818-61-1 | Nippon Shokubai |
| BHT | Butylated hydroxytoluene (food grade); CAS 000128-37-0 | Lanxess, BASF |
| DBTDL | Dibutyltin dilaurate; CAS 77-58-7 | Evonik |
| TPO | 2,4,6-trimethylbenzoyl diphenyl phosphine oxide; CAS 75980-60-8 | BASF |
| Card | Cardanol; CAS 37330-39-5 | Cardolite Chemical |
| Cyclohexane | Cyclohexane; CAS 110-82-7 | Idemitsu Kosan |
| 10% Pd/C | Palladium on carbon (10% palladium loading); CAS 7440-05-3 | Sigma Aldrich |
| Acrylic Acid | Acrylic acid; CAS 79-10-7 | BASF |
| DBT | di-t-butyl dicarbonate; CAS 24424-99-5 | Sigma Aldrich |
| LiBr | Lithium bromide; CAS 7550-35-8 | Sigma Aldrich |
| $MgSO_4$ | Magnesium sulfate; CAS 487-88-9 | Sigma Aldrich |
| T | Toluene; CAS 108-88-3 | SK Chemicals |
| MSA | Methanesulfonic acid; CAS 75-75-2 | Arkema |
| p-methoxy-phenol | Monomethyl ether hydroquinone | Kawaguchi |

Synthesis of Hydrogenated Cardanol (HCard)

4.51 g (15 mmol) of cardanol was mixed with 12 ml of cyclohexane and the heterogeneous catalyst 10% Pd/C (0.024 g Pd, 0.225 mmol). This mixture was placed in a 100 ml steel autoclave. The autoclave was locked, purged three times with argon (20 bar), two times with hydrogen (20 bar), and again with hydrogen (25 bar). The reaction mixture was then stirred (600 rpm) at room temperature for 2 hours, heated to 45° C., and hydrogenated at this temperature with continued stirring until the pressure had dropped to 7.5 bar (~24 hours). After cooling to room temperature, the obtained solution was filtered and the solvent was removed with a rotary evaporator. The remaining colorless oil solidified slowly on standing. Purification was performed two times via bulb-to-bulb distillation (205-220° C., 5×10−3 mbar) resulting in 3.32 g of hydrogenated cardanol (HCard) as a waxy solid. Measured H-NMR values for the obtained reaction mixture are as follows: H-NMR (400 MHz, CDCl3) δ 7.14 (t, J=7.6 Hz, 1H), 6.77-6.64 (m, 3H), 4.71 (broad s, 1H), 2.55 (t, J=8.0 Hz, 2H), 1.61-1.58 (m, 2H), 1.36-1.20 (m, 24H), 0.89 (t, J=7.4 Hz, 3H).

Synthesis of Hydrogenated Cardanol Acrylate (HCardA)

To make the acrylated iterant of HCard (the synthesis procedure for which is described in the preceding paragraph), a 500 mL round-bottom flask was successively charged with 50.0 g (368 mmol) of HCard, 26.5 g (368 mmol) of acrylic acid, 80.1 g (368 mmol) of di-t-butyl dicarbonate, 0.06 g (0.68 mmol) lithium bromide, and 0.06 g (0.68 mmol) magnesium sulfate. The resulting reaction mixture was then stirred for 24 hours at ambient temperature followed by dilution with 200 g hexane and washed three times with water. After completion of solvent evaporation using a rotary evaporator, the crude mixture was purified by silica gel column chromatography (hexane) yielding 62 g (81%) hydrogenated cardanol acrylate (HCardA) as a colorless liquid. Measured H-NMR values for the obtained reaction mixture are as follows: H NMR (400 MHz, CDCl3) δ 7.29-7.24 (m, 1H), 7.05-7.03 (m, 1H), 6.97-6.92 (m, 2H), 6.58 (d, J=17.3 Hz, 1H), 6.34-6.27 (m, 1H), 5.98 (d, J=11.4 Hz, 1H), 2.60 (t, J=7.8 Hz, 2H), 1.60-1.55 (m, 2H), 1.29-1.24 (m, 26H), 0.87 (t, J=7.0 Hz, 3H).

Synthesis of Ethoxylated Cardanol (EO5Card)

Cardanol 318 g (1 mol) and potassium hydroxide 0.05 g (0.006 mol) as a catalyst were charged in a 1 L autoclave equipped with a stirrer and cooling unit. After purging with nitrogen, the mixture was heated to 135° C. for 60 min. At that temperature, 220 g (5 mol) of ethylene oxide was added slowly at such a rate that the pressure rise was less than the gauge pressure (0.34 Mpa) and the temperature did not exceed 165° C. (for a period of 115 minutes in the instant case). After completing the ethylene oxide addition reaction, the temperature was maintained at 145° C. for 60 minutes. Next, the mixture was cooled to 60-70° C., after which it was neutralized with 0.38 g of acetic acid (0.006 mol). The resulting mixture was stirred for 30 minutes and then cooled down to room temperature. The reaction product resulted in 505 g of EOCard with an average of 4.95 degrees of ethoxylation. Measured H-NMR values for the mixture are as follows: H NMR (400 MHz, CDCl3) δ 7.19-7.17 (m, 1H), 6.77-6.71 (m, 3H), 5.69-5.33 (m, 2H), 4.13-3.61 (m, 19.8H), 2.55 (t, J=7.7 Hz, 2H), 2.15-1.99 (m, 4H), 1.79-1.54 (m, 6H), 1.42-1.18 (m, 16H), 0.88 (m, 3H).

Synthesis of Ethoxylated Hydrogenated Cardanol (EO5HCard)

First, 318 g (1 mol) of hydrogenated cardanol (HCard as described above) was charged with 0.05 g (0.006 mol) of potassium hydroxide 0.05 g in a 1 L autoclave equipped with a stirrer and cooling unit. After purging the mixture with nitrogen, it was heated to 135° C. for 60 min. At that temperature, 220 g (5 mol) ethylene oxide was added slowly at such a rate that the pressure rise was less than the gauge pressure 0.34 MPa and the reaction temperature not exceed 165° C. (for a period of approximately 2 hours in the instant case). After completing the ethylene oxide addition reaction, the reaction temperature was maintained at 145° C. for 60 minutes. Next, the mixture was cooled to 60-70° C., after which it was neutralized with 0.38 g of acetic acid (0.006 mol). The resulting mixture was stirred for 30 minutes and subsequently cooled to room temperature. The reaction product resulted in 500 g of EOHCard with an average degree of ethoxylation of 4.95. Measured H-NMR values for the mixture are as follows: H NMR (400 MHz, CDCl3) δ 7.19-7.15 (m, 1H), 6.80-6.74 (m, 3H), 4.15-3.63 (m, 19.6H), 2.58 (t, J=8.0 Hz, 2H), 1.81-1.18 (m, 26H), 0.90 (m, 3H).

Synthesis of Ethoxylated Hydrogenated Cardanol (EO1H Card)

First, 318 g (1 mol) of hydrogenated cardanol (HCard as described above) was charged with 0.05 g (0.006 mol) of potassium hydroxide 0.05 g in a 1 L autoclave equipped with a stirrer and cooling unit. After purging the mixture with nitrogen, it was heated to 135° C. for 60 min. At that temperature, 44 g (1 mol) ethylene oxide was added slowly at such a rate that the pressure rise was less than the gauge pressure 0.34 MPa and the reaction temperature not exceed 165° C. (for a period of approximately 2 hours in the instant case). After completing the ethylene oxide addition reaction, the reaction temperature was maintained at 145° C. for 60 minutes. Next, the mixture was cooled to 60-70° C., after which it was neutralized with 0.38 g of acetic acid (0.006 mol). The resulting mixture was stirred for 30 minutes and subsequently cooled to room temperature. The reaction product resulted in 360 g of EO1HCard. Measured H-NMR values are as follows: H NMR (400 MHz, CDCl3) δ 7.19-7.15 (m, 1H), 6.80-6.74 (m, 3H), 4.33 (t, 2H, J=7 Hz), 3.7 (t, 2H, J=7 Hz), 2.58 (t, J=8.0 Hz, 2H), 1.81-1.18 (m, 26H), 0.90 (m, 3H).

Synthesis of Propoxylated Hydrogenated Cardanol (PO6HCard)

First, 30.1 g (0.09 mol) of hydrogenated cardanol (HCard as described above), along with 59.5 mL (0.85 mol) of propylene oxide, and 3.0 g of $Al_2O_3$—MgO were added into a 500 ml stainless steel autoclave equipped with a mechanical stirred and heater. After purging the mixture with $N_2$ five times, the reaction mixture was heated to 120° C. for 8 hours while stirring. After this, the reaction mixture was cooled to room temperature. Finally, the catalyst was separated by washing the mixture with ethanol. The resulting reaction product was a 70 g of a yellow liquid POHCard with an average degree of propoxylation of 6.3. Measured H-NMR values for the mixture are as follows: H NMR (400 MHz, CDCl3) δ 7.16 (t, J=7.5 Hz, 1H), 6.77-6.70 (m, 3H), 3.93-3.15 (m, 18.9H), 2.56 (t, J=7.9 Hz, 2H), 1.63-1.08 (m, 44.9H), 0.88 (t, J=7.0 Hz, 3H).

Synthesis of Ethoxylated Hydrogenated Cardanol Acrylate (EO5HCardA)

A 500 ml round bottom flask equipped with a Dean-Stark set-up was charged with 77.9 g (150 mmol) of EO5HCard (as described above), 31 ml of cyclohexane, 16 ml of toluene, 13.5 g of (188 mmol) acrylic acid, 0.64 g of methanesulfonic acid and 0.13 g of monomethyl ether hydroquinone (p-methoxyphenol). The reaction mixture was refluxed with azeotropic removal of water until the acid value remained constant. Next, the reaction mixture was cooled to room temperature, after which 44 g of a 15% aqueous sodium hydroxide solution was added, followed by a washing with water. After filtration and evaporation of the solvents, 61.9 g (72%) of EO5HCardA was obtained. Measured H-NMR values for the mixture are as follows: H NMR (400 MHz, CDCl3) δ 7.18-7.15 (m, 1H), 6.77-6.71 (m, 3H), 6.42 (d, J=13.9 Hz, 1H), 6.18-6.12 (m, 1H), 5.84-5.81 (m, 1H), 4.31-3.64 (m, 19.6H), 2.55 (t, J=6.3 Hz, 2H), 1.98-1.20 (m, 26H), 0.87 (t, J=5.4 Hz, 3H).

Synthesis of Ethoxylated Hydrogenated Cardanol Acrylate (EO1HCardA)

This synthesis was performed similar to described for EO5HCardA using the same molar amounts, except that EO1HCard (as described above) was applied instead of EO5HCard. Measured H-NMR values are as follows: H NMR (400 MHz, CDCl3) δ 7.18-7.15 (m, 1H), 6.77-6.71 (m, 3H), 6.42 (d, J=13.9 Hz, 1H), 6.18-6.12 (m, 1H), 5.84-5.81 (m, 1H), 4.51 (t, 2H, J=5 Hz), 4.20 (t, 2H, J=5 Hz), 2.56 (t, J=6.3 Hz, 2H), 1.98-1.20 (m, 26H), 0.87 (t, J=5.4 Hz, 3H).

Synthesis of Propoxylated Hydrogenated Cardanol Acrylate (PO6HCardA)

A 500 ml round bottom flask equipped with a Dean-Stark set-up was charged with 100.2 g (150 mmol) of PO6HCard (as described above), 40 ml of cyclohexane, 20 ml of toluene, 13.2 g (184.5 mmol) of acrylic acid, 0.75 g of methanesulfonic acid (MSA), and 0.16 g of monomethyl ether hydroquinone (p-methoxyphenol). The reaction mixture was refluxed with azeotropic removal of water until the acid value remained constant. Next, the reaction mixture was cooled to room temperature, after which 63 g of a 15% aqueous sodium hydroxide solution was added, followed by washing with water. After filtration and evaporation of the solvents, 72.5 g (68%) of PO6HCardA was obtained. Measured H-NMR values for the mixture are as follows: H NMR (400 MHz, CDCl3) δ 7.16 (t, J=7.7 Hz, 1H), 6.77-6.70 (m, 3H), 6.39 (d, J=17.3 Hz, 1H), 6.15-6.08 (m, 1H), 5.81-5.78 (m, 1H), 5.11-5.08 (m, 1H), 3.98-3.20 (m, 18.9H), 2.56 (t, J=7.9 Hz, 2H), 1.62-1.12 (m, 44.9H), 0.88 (t, J=7.0 Hz, 3H).

Synthesis of Oligomer 1

To synthesize Oligomer 1, first, 95.35 parts of PPG8000 was charged into a 250 ml reactor (equipped with a stirrer, air inlet, dropping funnel, and condenser). After charging, the reactor was heated to 45° C. before the reactor was purged with dry lean air. Then 3.13 parts of TDI was charged into the reactor whilst stirring. After this step 0.03 parts of DBTDL was added into the reactor. After waiting one (1) hour for the reaction to commence, the temperature was then raised to 60° C. The 60° C. temperature was then further maintained for two (2) additional hours. After this two (2) additional hours of reaction time, the quantity of isocyanate (NCO) content was measured by a potentiometric titrator to ensure it was within 10% of the value of the theoretical isocyanate content. If the measured value was not within 10%, the reaction was allowed to continue in additional 15-minute increments and then rechecked until such value was achieved. Upon confirmation of the appropriate isocyanate content, 1.39 parts of HEA was added to the mixture, together with the specified amount of 0.15 parts BHT. Next the temperature was raised to 85° C. The resulting mixture was reacted for one (1) additional hour at 85° C. After allowing for this additional one (1) hour of reaction time, the NCO content was checked via potentiometric titration again. Once the isocyanate content was lower than 0.1% relative to the entire weight of the composition the reaction was considered finished. If the isocyanate content was not lower than this value, the mixture was placed back in the reaction chamber in 15-minute additional increments (again at 85° C.) and checked again, with this step repeated until the isocyanate content fell to within the desired range. Finally, the resulting synthesized oligomer was cooled slowly and discharged for use in the experiments described elsewhere herein. The resulting Oligomer 1 possesses a theoretical Mn ($Mn_{theo}$) of 16754. Based on GPC (HFIP, triple detector SEC), Oligomer 1 as synthesized above was observed to possess an Mn of 15700, an Mw of 23600, and an Mz of 34800 (all values in g/mol).

H-NMR

In the synthesis procedures described above, all H-NMR measurements were performed sing a Bruker AV-III 400 NMR Spectrometer (400 MHz) employing $CDCl_3$ solvent.

SEC

As applicable, various components were evaluated according to the size exclusion chromatography (SEC) method in accordance with ASTM: D5296-11: "Standard Test Method for Molecular Weight Averages and Molecular Weight Distribution of Polystyrene by High Performance Size-Exclusion Chromatography," ASTM International, West Conshohocken, PA, (2011). Additionally, ASTM norm D 5226-98: "Standard Practice for Dissolving Polymer Materials," ASTM International, West Conshohocken, PA, (2010), was used to facilitate the definition of solvents which are appropriate for polymer analysis.

Specifically, all Size Exclusion Chromatography measurements were performed on a Viscotek GPCMax VE2001 solvent/sample module system, further equipped with a TDA302 triple detector array. For chromatographic separation, 3 PFG linear XL columns from PSS Polymer Standards Service GmbH were used. Detectors and columns were operated at 35° C. Prior to conducting SEC, with a single exception, each respective polymer was dissolved at a concentration ranging from 1.0 to 1.5 mg/ml in hexafluoroisopropanol (HFIP) containing 0.1 wt. % of potassium trifluoroacetate, which potassium trifluoroacetate was also used as an eluent in SEC analysis at a flow rate of 0.8 ml/min.

With the dissolution complete, the molar mass and molar mass distribution were then determined with the above-referenced triple detection method using the refractive index, differential viscosity and right-angle light scattering signals. For a calculation of molecular weight averages and molar mass distribution, a fixed refractive index increment (dn/dc) of 0.215 ml/g was used. The refractive index increment and molecular mass averages, as well as the molar mass distributions were determined by integration of the whole refractive index chromatograms. An IV-DP signal was additionally used to set the integration limit. Recoveries of the samples from columns varied between 95 and 105%, which are the typical of values obtained in size-exclusion chromatography.

Using the above-prescribed method, values for number-average molecular weight (Mn), weight-average molecular weight (Mw), peak molecular weight (Mp), and Z-average molecular weight (Mz) were recorded. The theoretical molecular weight (Mn, theo), which can be determined via computation based upon well-known methods using publicly available.

Viscosity

Viscosities of the formulations were determined using an Anton Paar MCR702rheometer equipped with a P-PTD200 heating device for use with a parallel plate system using a 25 mm parallel plate. For the solvent a C-PTD200 heating device, DG26.7 double gap geometry in combination with solvent trap was used.

Formulations

Each of the formulations indicated in Tables 2A and 2B below were prepared by using a 50 ml mixing cup suitable for use with a Speedmixer™. Specifically, for each formulation, 1 part by weight of the photoinitiator TPO was added to 70 parts of Oligomer 1 (the synthesis procedure for which is described above), followed by 30 parts of the monomer as indicated in the relevant table, resulting in 10.1 g in total. The cup was then closed and vigorously mixed in a Speedmixer™ DAC150FVZ 30 seconds, stopped, and mixed again for 30 additional seconds via the same method.

These samples were tested according to the methods described below for determining each formulation's, the $T_{30\%,\ modulus\ max}$, and Max. Modulus G', respectively. Values for these measured characteristics are reported in Tables 2A-2B below.

Determination of Maximum Modulus (G') and $T_{30\%,\ modulus\ max}$ values

Values for Maximum Modulus (G') were determined according to the following procedure described herein. The hardware/equipment used in this procedure was as follows:

Rheometer+Accessories
- ARESG2-rheometer (manufacturer: TA Instruments)
- APS temperature control device (Advanced Peltier System)
- APS Standard Flat Plate (lower geometry)
- ARESG2 UV-curing Accessory (upper plate fixture, UV-light shield back & access door, collimating optic lens)
- Ø20 mm acrylic plate with the UV-curing Option upper plate fixture (upper geometry)
- Silverline UV radiometer, UV-light sensor (non-calibrated), UV-sensor geometry and disposable plate holder UV-Light Source & Other
- Omnicure LX500 in combination with 385 nm LED and 8 mm lens attached
- Moeller Easy 412-DC-TC Control Relay (trigger box)
- UV Power Puck II (Electronic Instrumentation & Technology, calibrated)

The hardware described above was then set-up and arranged according to the following. First, UV-curing measurements were performed on the ARESG2 rheometer (TA Instruments). The rheometer was equipped with the APS temperature control device, the APS Standard Flat Plate as lower geometry and the ARESG2 UV-curing Option. The upper geometry used was the upper plate fixture from the ARESG2 UV-curing Option in combination with a 20 mm diameter acrylic plate. As the UV-light source, the Omnicure LX500 spot curing system was used in combination with 385 nm LED (8 mm lens). The 385 nm LED was then inserted into the collimating optic lens of the ARES G2 UV-curing accessory. The collimating lens was fixed to the light shield and aligned to the upper UV geometry mirror and the alignment screws were tightened. The diameter of the original 5 mm lightguide holder part of the collimating lens was increased to 12 mm in order to accommodate the 385 nm UV-LED.

Then, the Omnicure LX500 spot curing system was connected via a Moeller Easy 412-DC-TC Control Relay to the DIGITAL I/O connector at the ARESG2. The Control Relay served as a trigger-box for the UV-light source. The delay time of the trigger was set to 1.5 seconds, meaning that the 385 nm UV-LED was automatically switched on with a delay of 1.5 seconds after the start of the data collection of the modulus measurement on the ARESG2. The light intensity was set to 95%, and the duration of the UV-light was fixed to 128 seconds.

Alignment of the UV-light: Alignment was performed prior to installation of the APS temperature control unit. The UV sensor geometry was attached to a disposable plate holder and installed as the lower geometry. The UV-light sensor, which was connected to Silverline UV-radiometer, was positioned in the outer hole of the UV sensor geometry. The upper geometry was positioned on top of the UV-light sensor by applying approximately 100 grams of axial force. Then, the light intensity was measured at four locations by rotating the lower geometry approximately 900 between each successive measurement. In order to achieve a light distribution at each point which was as equal as possible, the alignment of the collimating lens was then adjusted with the alignment screws on the light shield. The difference in light intensity at the four different positions was maintained to below 10%.

Determination of Light Intensity: Prior to the RT-DMA measurements, the UV-intensity was measured with help of a calibrated UV Power Puck II. To achieve this, the sensor of the UV Power Puck II was positioned directly below the surface of the 20 mm acrylic plate in the upper plate fixture (distance <0.5 mm) with the surface of the acrylic plate completely covering the sensor surface. Next, the Omnicure LX500 UV-source (with an intensity value set to 95%) was manually switched on for 10 seconds. During this 10 second interval, the UVA2 intensity (i.e. radiation between wavelengths of 380-410 nm) was measured with the UV Power Puck II instrument. The measured UVA2 intensity was determined to be between 60-70 $mW/cm^2$, with an actual value of 67 $mW/cm^2$ recorded.

Determination of the actual delay time: When starting a measurement, there was a delay between the start of data sampling and the start of UV-illumination. In the settings of the Moeller Easy 412-DC-TC Control Relay, the delay was set to 1.5 seconds, which signifies that the UV-illumination began 1.5 seconds after the initiation of data sampling.

With help of a Light Dependent Resistance (LDR) and an oscilloscope (PicoScope 3424) an actual delay time of 1.519 s was measured. The delay time of 1.519 seconds was the measured average value of 10 individual measurements with a standard deviation of 0.004 seconds.

RT-DMA measurement: The RT-DMA UV-curing measurements were then performed using an ARESG2 rheometer paired with the Advanced Peltier System as a temperature control device, the APS Flat Plate, and the ARESG2 UV-curing Accessory set up. A 385 nm LED with an 8-mm lens connected to the Omnicure LX500 was used as the UV light source.

Sample loading: Prior to loading each respective sample, the temperature of the bottom plate was set to 50° C. When the temperature reached 50° C., the surface of the upper plate (which was an acrylic plate with a thickness of 20 mm) was brought into contact (i.e. a gap of 0 mm with the lower plate by applying an axial force of between 200-400 grams, thereby allowing the upper parallel plate to equilibrate to the set temperature of 50° C. The system was allowed to further equilibrate its temperature for at least 5 minutes after initial contact. Next, a zero-fixture procedure was performed according to well-known methods to determine the gap=0 position. After determining the gap=0 position, the upper plate was moved to a position of 10 mm away. Then a portion of each respective sample was transferred to the center of the lower plate with the tip of a small spatula, after which the upper geometry was lowered to a gap=0.120 mm position. The quantity of the sample had to be sufficient to ensure than an excess would be pushed outside of the gap covering the entire circumference of the upper parallel plate after the upper geometry was brought down to the reduced gap. Next, the excess of sample that had been displaced outside of the gap was removed, and the upper geometry was brought down further to the measuring position (having a gap=0.100 mm). With the measuring position loaded, the temperature of the sample was allowed to equilibrate to 50° C. Finally, when the sample temperature was measured as stable between 49.9° and 50.10° C., the measurement process would commence by activating the trigger box (Moeller Easy 412-DC-TC) and using the interface and interconnection provided by the TRIOS software package.

Measurement: The actual UV cure RT-DMA measurement was a so-called "fast sampling" measurement taken at 50° C. That is, it was an oscillation fast sampling taken at 50° C. for a duration of 128 seconds, with a 1% strain, a rotational velocity of 52.36 rad/s, and a measurement frequency of 50 points per second (i.e. 0.020 seconds between each successive measurement point).

Then, the measurement was started via the start button in the TRIOS software. Once the data sampling started, the rheometer sent a signal to the control relay, which in turn activated the Omnicure LX500 UV-light source to illuminate the respective sample with the aforementioned delay of 1.519 s after commencement of data sampling. The sample was illuminated with the 385 nm UV-light (Intensity 60-70 $mW/cm^2$) during 128 seconds of fast sampling data collection as described above. After the measurement was finished, the TRIOS data file was exported to Microsoft Excel. Then the sample was removed and the plates subsequently cleaned thoroughly with ethanol prior to loading of the next sample.

Data analysis: As mentioned, the TRIOS data was exported to Microsoft Excel. Excel was used to plot graphs and calculate various parameters for characterization of the cure speed performance of the tested formulations as described below. The graphs included those corresponding to storage modulus (G') as a function of UV-time (UV-time was calculated by subtracting the delay time (1.519 s) from the actual time for each individual data point), and relative storage modulus (rel G') as function of UV-time (rel G' was calculated by the quotient of the measured G' value at certain UV-time and the maximum obtained G' value during the cure measurement). The maximum value observed of the graph of the G' graph was determined by taking the average of the G' value between 110 and 120 seconds, and is reported in Tables 2A and 2B and 3 below under the column headed by "Max. G'". For samples that did not fully cure during the testing time, this column is indicated with the designation "NFC," indicating a Max. G' was not attainable given the test procedure and time limits employed.

The characteristic parameters, meanwhile, included: (1) the time to reach 30% of the total storage modulus (G') increase, and (2) average G' 110-120 s (Average storage modulus value out of 6 datapoints towards the end of the cure measurement). The results for (1) of each formulation is reported in Tables 2A-2B below under the column headed by $T_{30\%,\ modulus\ max}$.

TABLE 2A

| Results for Formulations 1, 2, A, B and C | | | |
|---|---|---|---|
| Formu-lation | | $T_{30\%, modulus\ max\ (seconds)}$ | Max G` (MPa) |
| 1 | EO5HCardA | 0.71 | 0.28 |
| 2 | PO6HCardA | 0.74 | 0.25 |
| A | EO1HcardA | 0.97 | 0.26 |
| B | Ethoxylated (EO)4 phenol acrylate | 1.05 | 0.33 |
| C | Phenoxy ethyl acrylate | 0.95 | 0.30 |

TABLE 2B

| Results for Formulations D-H | | | |
|---|---|---|---|
| Formu-lation | | $T_{30\%, modulus\ max\ (seconds)}$ | Max G` (MPa) |
| D | 2-ethyl hexyl acrylate | 2.1 | 0.21 |
| E | Tetrahydrofurfuryl acrylate | 1.1 | 0.37 |
| F | t-butyl cyclohexyl acrylate | 0.9 | 0.25 |
| G | EOEOA Ethyl diethyl-enegylcol acrylate | 1.2 | 0.26 |

These examples and comparative experiments demonstrate the high speed and good modulus development of the alkoxylated hydrogenated cardanol acrylates according to the invention. The higher cure speed for the higher degree of alkoxylation is especially surprising when considering phenoxy ethyl acrylate (C) and ethoxylated (EO)4 phenol acrylate (B). Here increasing the degree of ethoxylation resulted in a reduction in cure speed.

TABLE 3

| Viscosities | | | | | |
|---|---|---|---|---|---|
| Formu-lation | | Visco 25° C. (Pa · s) | Visco 55° C. (Pa · s) | Ratio Visco 55° C./25° C. | Max G` (MPa) |
| 1 | EO5HCard A (molecular weight 578) | 28 | 7.1 | 0.25 | 0.28 |
| H | Ethoxylated (EO)4 nonyl phenol acrylate (molecular weight 450) | 33 | 7.4 | 0.22 | 0.27 |

This table demonstrates the excellent cutting power of alkoxylated hydrogenated cardanol acrylates according to the invention. Despite the fact that the molecular weight of EOSHCardA is higher than of ENPA, which normally results in higher viscosities, the formulation with EO5HCardA surprisingly has a lower viscosity at 25° C. Another surprising effect is the fact that the viscosity is also less sensitive to temperature increases as indicated by the viscosity ratio (55° C./25° C.).

As can be seen, the tables above show that cardanol-based reactive diluents according to the present invention exhibit one or more superior properties to their comparative analogues. The foregoing suggests that reactive diluent monomers according to various aspects of the present invention tend to possess properties which would make them especially suitable for use in various UV-curing applications.

Additional Exemplary Aspects and Embodiments

A First Additional Exemplary Aspect Includes One or More of the Following Embodiments:

1. A compound of the following formula (Ia):

(Ia)

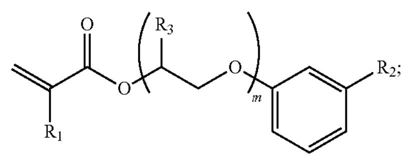

wherein $R_1$ is H or $CH_3$;

$R_2$ is a $C_Y$ alkyl chain having a number of H atoms defined by the expression X(2Y+1); wherein Y is from 9 to 15 and X is from 0.93 to 1.0;

$R_3$ is H or a $C_1$-$C_4$ alkyl chain, more preferably H or $CH_3$; and m is at least 3, preferably at least 4 and m is at most 9, preferably at most 8, more preferably at most 7, even more preferably at most 6, even more preferably at most 5.

2. A compound according to formula (Ia), wherein the compound is a cardanol-derived monomer.
3. A compound according to additional exemplary embodiments 1-2, wherein the compound is a cardanol-derived monomer which is obtained from a cashew nut shell liquid.
4. A compound according to any of the previous additional exemplary embodiments, wherein m is from 3 to 9.
5. A compound according to any of the previous additional exemplary embodiments, wherein m is from 3 to 8, or from 3 to 7, or from 3 to 6, or from 3 to 5, or from 4 to 9, or from 4 to 8, or from 4 to 7, or from 4 to 6, or m is 4 or 5.
6. A compound according to any of the previous additional exemplary embodiments, wherein X is greater than 0.93, or greater than 0.99 or X is 1.0.
7. A compound according to any of the previous additional exemplary embodiments, wherein the compound possesses a number average molecular mass, as measured by a suitable method such as size exclusion chromatography (SEC) method, from 400-800 g/mol, or from 400-770 g/mol, or from 400-750 g/mol, or from 450-750 g/mol, or from 500-750 g/mol.
8. A compound according to any of the previous additional exemplary embodiments, wherein the compound is fully hydrogenated.
9. A compound according to any of the previous additional exemplary embodiments, wherein Y equals 15.
10. A compound according to any of the previous additional exemplary embodiments, wherein the compound, when incorporated into a composition containing 30 parts per weight of the compound, 1 part per weight of the photoinitiator TPO, and 70 parts per weight of Oligomer 1 (as defined elsewhere herein), and subjected to cure conditions as described elsewhere herein, exhibits $T_{30\%, modulus\ max}$ of less than 1 second, or less than 0.9 seconds (s), or less than 0.8 s, or from 0.5 to 1.0 s, or from 0.6 to 1.0 s, or from 0.6 to 0.9 s, or from 0.7 to 1.0 s, or from 0.7 to 0.9 s, wherein $T_{30\%, modulus\ max}$ is measured according to a method as described elsewhere herein.

A second additional exemplary aspect includes one or more of the following embodiments:

1. A composition or mixture comprising, consisting of, or consisting essentially of compound(s) according to formula (Ia):

(Ia)

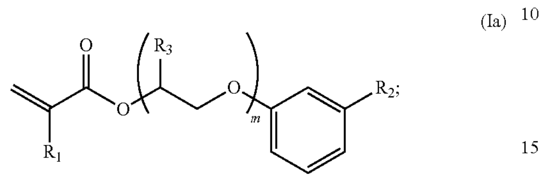

wherein $R_1$ is H or $CH_3$;

$R_2$ is a $C_Y$ alkyl chain having a number of H atoms defined by the expression X(2Y+1); wherein Y is from 9 to 15 and X is from 0.93 to 1.0;

$R_3$ is H or a $C_1$-$C_4$ alkyl chain, more preferably H or $CH_3$; and m is at least 3, preferably at least 4 and m is at most 9, preferably at most 8, more preferably at most 7, even more preferably at most 6, even more preferably at most 5;

wherein the composition or mixture comprises at least 20 wt. %, or at least 30 wt. %, or at least 40 wt. %, or at least 50 wt. %, or from 20-80 wt. %, or from 20-70 wt %, or from 20-60 wt. %, or from 20-50 wt. %, or from 30-80 wt. %, or from 30-60 wt. %, or from 40-80 wt. %, or from 40-60 wt. % of biobased content, wherein biobased content may be determined by a suitable method such as in accordance with ISO 16620-2:2019.

2. A composition or mixture comprising, relative to the entire weight of the composition or mixture, at least 90%, or at least 95%, or at least 98%, or at least 99%, or from 90-99% by weight of compounds according to formula (Ia), wherein formula (Ia) is further limited such that Y equals 15 and X equals 1.0.

2. A composition or mixture comprising, consisting of, or consisting essentially of reactive diluents, wherein the composition or mixture comprises a purity of least 50%, or at least 65%, or at least 80%, or at least 90%, or at least 95%, or at least 98%, or at least 99%, or from 50-99%, or from 80-99%, or from 50-95%, or from 65-95%, or from 80-95%, or from 90-100%, or from 90-99.9%, or from 90-99%; wherein purity is defined as a percentage by weight, relative to the weight of the entire composition or mixture, of compounds according to formula (Ia); wherein purity is measured by a suitable method such as a size exclusion chromatography (SEC) method.

3. The composition or mixture of the previous exemplary embodiment 2, wherein the reactive diluents comprise, consist of, or consist essentially of cardanol-derived reactive diluents.

4. A composition or mixture according to the previous exemplary embodiment 3, wherein the cardanol-derived diluents are derived from cardanol which is obtained from a cashew nut shell liquid.

5. A composition or mixture according to any of the previous embodiments 1-4 of the second additional exemplary aspect, wherein m is from 3 to 9.

6. A composition or mixture according to any of the previous embodiments 1-4 of the second additional exemplary aspect, wherein m is from 3 to 8, or from 3 to 7, or from 3 to 6, or from 3 to 5, or from 4 to 9, or from 4 to 8, or from 4 to 7, or from 4 to 6, or m is 4 or 5.

7. A composition or mixture according to any of the previous embodiments 1-6 of the second additional exemplary aspect, wherein X is greater than 0.93, or greater than 0.99.

8. A composition or mixture according to any of the previous embodiments 1-7 of the second additional exemplary aspect, wherein the composition or mixture possesses a number average molecular mass, as measured by a suitable method such as size exclusion chromatography (SEC) method, from 400-800 g/mol, or from 400-770 g/mol, or from 400-750 g/mol, or from 450-750 g/mol, or from 500-750 g/mol.

9. A composition or mixture according to any of the previous embodiments 1-8 of the second additional exemplary aspect, wherein the composition or mixture is fully hydrogenated.

10. A composition or mixture according to any of the previous embodiments 1-9 of the second additional exemplary aspect, wherein Y equals 15.

11. A composition or mixture according to any of the previous embodiments 1-10 of the second additional exemplary aspect, wherein the composition or mixture, when incorporated into a broader composition containing 30 parts per weight of the composition or mixture, 1 part per weight of the photoinitiator TPO, and 70 parts per weight of Oligomer 1 (as defined herein), and subjected to cure conditions as described elsewhere herein, exhibits $T_{30\%, modulus\ max}$ of less than 1 second, or less than 0.9 seconds (s), or less than 0.8 s, or from 0.5 to 1.0 s, or from 0.6 to 1.0 s, or from 0.6 to 0.9 s, or from 0.7 to 1.0 s, or from 0.7 to 0.9 s, wherein $T_{30\%, modulus\ max}$ is measured according to a method as described elsewhere herein.

12. A composition or mixture according to any of the previous embodiments 1-12 of the second additional exemplary aspect, wherein the composition or mixture is substantially solvent-free, or substantially water-free, or contains less than 1 wt. % of solvent and/or less than 1 wt. % of water, or less than 0.5 wt. % of solvent and/or less than 0.5 wt. % of water, or less than 0.1 wt. % of solvent and/or less than 0.1 wt. % of water, wherein the weight content of water may be determined via a Karl Fischer titration method, and the weight content of non-water solvents may be determined via a size exclusion chromatography (SEC) method.

13. A composition or mixture according to any of the previous embodiments 1-12 of the second additional exemplary aspect, wherein the composition or mixture consists of or consists essentially of the product(s) of the reaction(s) leading to the compounds according to formula (Ia).

A third additional exemplary aspect includes one or more of the following embodiments:

1. A UV-curable composition containing at least 0.1 wt. %, or at least 0.5 wt. %, or at least 1 wt. %, or at least 5 wt. %, or at least 10 wt. %, or at least 25 wt. %, or at least 50 wt. % of a first diluent monomer component, wherein the first diluent monomer component consists of compounds according to formula (Ia):

(Ia)

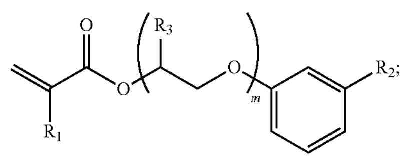

wherein $R_1$ is H or $CH_3$;

$R_2$ is a $C_Y$ alkyl chain having a number of H atoms defined by the expression X(2Y+1); wherein Y is from 9 to 15 and X is from 0.93 to 1.0;

$R_3$ is H or a $C_1$-$C_4$ alkyl chain, more preferably H or $CH_3$; and m is at least 3, preferably at least 4 and m is at most 9, preferably at most 8, more preferably at most 7, even more preferably at most 6, even more preferably at most 5.

2. A UV-curable composition according to the previous embodiment of the third additional exemplary aspect, wherein the first diluent monomer component comprises at least 20 wt. %, or at least 30 wt. %, or at least 40 wt. %, or at least 50 wt. %, or from 20-80 wt. %, or from 20-70 wt %, or from 20-60 wt. %, or from 20-50 wt. %, or from 30-80 wt. %, or from 30-60 wt. %, or from 40-80 wt. %, or from 40-60 wt. % of biobased content, wherein biobased content may be determined by a suitable method such as in accordance with ISO 16620-2:2019.

3. A UV-curable composition according to the first or second embodiments of the third additional exemplary aspect, wherein the first diluent monomer component comprises at least 90%, or at least 95%, or at least 98%, or at least 99%, or from 90-100%, or from 90-99.9%, or from 90-99% by weight of compounds according to formula (Ia), wherein formula (Ia) is further limited such that Y equals 15 and X equals 1.0.

4. A UV-curable composition according to any of embodiments 1-3 of the third additional exemplary aspect, wherein the first diluent monomer component comprises a purity of least 50%, or at least 65%, or at least 80%, or at least 90%, or at least 95%, or at least 98%, or at least 99%, or from 50-99%, or from 80-99%, or from 50-95%, or from 65-95%, or from 80-95%, or from 90-100%, or from 90-99.9%, or from 90-99%; wherein purity is defined as a percentage by weight, relative to the weight of the entire first diluent monomer component, of compounds according to formula (Ia); wherein purity is measured by a suitable method such as a size exclusion chromatography (SEC) method.

5. A UV-curable composition according to any of embodiments 1-4 of the third additional exemplary aspect, wherein the first diluent monomer component comprises, consists of, or consists essentially of cardanol-derived reactive diluents.

6. A UV-curable composition according to the previous embodiment, wherein the cardanol-derived diluents are derived from cardanol which is obtained from a cashew nut shell liquid.

7. A UV-curable composition according to any of embodiments 1-6 of the third additional exemplary aspect, wherein the UV-curable composition further comprises a second diluent monomer component.

8. A UV-curable composition according to any of embodiments 1-7 of the third additional exemplary aspect, wherein m is from 3 to 9.

9. A UV-curable composition according to any of embodiments 1-7 of the third additional exemplary aspect, wherein m is from 3 to 8, or from 3 to 7, or from 3 to 6, or from 3 to 5, or from 4 to 9, or from 4 to 8, or from 4 to 7, or from 4 to 6, or m is 4 or 5.

10. A UV-curable composition according to any of embodiments 1-9 of the third additional exemplary aspect, wherein X is greater than 0.93, or greater than 0.99.

11. A UV-curable composition according to any of embodiments 1-10 of the third additional exemplary aspect, wherein the first diluent monomer component possesses a number average molecular mass, as measured by a suitable method such as size exclusion chromatography (SEC) method, from 400-800 g/mol, or from 400-770 g/mol, or from 400-750 g/mol, or from 450-750 g/mol, or from 500-750 g/mol.

12. A UV-curable composition according to any of embodiments 1-11 of the third additional exemplary aspect, wherein X=1.0.

13. A UV-curable composition according to any of embodiments 1-12 of the third additional exemplary aspect, wherein Y equals 15.

14. A UV-curable composition according to any of embodiments 1-13 of the third additional exemplary aspect, wherein the UV-curable composition is substantially solvent-free, or substantially water-free, or contains less than 1 wt. % of solvent and/or less than 1 wt. % of water, or less than 0.5 wt. % of solvent and/or less than 0.5 wt. % of water, or less than 0.1 wt. % of solvent and/or less than 0.1 wt. % of water, wherein the weight content of water is determined via a Karl Fischer titration method, and the weight content of non-water solvents may be determined via a size exclusion chromatography (SEC) method.

A fourth additional exemplary aspect includes one or more of the following embodiments:

1. A method comprising the steps of:
   (a) providing a cardanol, preferably a cardanol derived from a CNSL, wherein the cardanol comprises a phenol group and an alkyl chain;
   (b) alkoxylating the phenol group of the cardanol;
   (c) subjecting the cardanol to a hydrogenation step, such that the alkyl chain is at least 93%, preferably at least 99% hydrogenated; and
   (d) esterifying the cardanol with a (meth)acrylic acid to functionalize it with a single (meth)acrylate group;

wherein steps (b) and (c) are interchangeable.

2. A method according to the previous embodiment, wherein the method is configured to produce a compound according to any of the embodiments of the first additional exemplary aspect, a composition or mixture according to an of the embodiments of the second additional exemplary aspect, or a first reactive diluent component according to any of the embodiments of the third additional exemplary embodiment.

Unless otherwise specified, the term wt. % means the amount by mass of a particular constituent relative to the entire liquid radiation curable composition into which it is incorporated.

The use of the terms “a” and “an” and “the” and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the invention has been described in detail and with reference to specific embodiments thereof, it will be apparent to one of ordinary skill in the art that various changes and modifications can be made therein without departing from the spirit and scope of the claimed invention.

What is claimed is:

1. A compound for use in a UV-curable composition of the following formula (Ia):

(Ia)

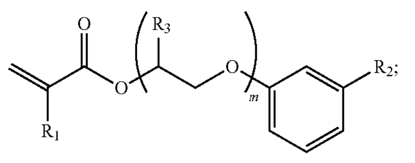

wherein $R_1$ is H or $CH_3$;

$R_2$ is a $C_Y$ alkyl chain having a number of H atoms defined by the expression X(2Y+1);

wherein Y is from 9 to 15 and X is from 0.93 to 1.0;

$R_3$ is H or a $C_1$-$C_4$ alkyl chain; and m is from 3 to 8.

2. The compound of claim 1, wherein the compound is a cardanol-derived monomer.

3. The compound of claim 2, wherein the cardanol-derived monomer is obtained from a cashew nut shell liquid (CNSL).

4. The compound according to claim 1, wherein Y is 15.

5. The compound according to claim 4, wherein X is 1.0.

6. The compound according to claim 1, wherein m is from 4 to 8.

7. A composition or mixture comprising the compound of claim 1, wherein the composition or mixture comprises at least 20 wt. % of biobased content, wherein biobased content is determined in accordance with ISO 16620-2: 2019.

8. A UV-curable composition containing at least 0.1 wt. % of a first diluent monomer component, relative to the weight of the entire composition, wherein the first diluent monomer component consists of (i) the compound according to claim 1 and/or (ii) the composition or mixture according to claim 7.

9. The UV-curable composition according to claim 8, wherein the UV-curable composition contains less than 1 wt. % of solvent or less than 1 wt. % of water, wherein the weight content of water is determined via a Karl Fischer titration method or an SEC method.

10. The UV-curable composition according to claim 8, wherein the UV-curable composition further comprises (a) one or more oligomers having one or more ethylenically unsaturated groups, and (b) a photoinitiator, (c) optionally, one or more additives.

11. The UV-curable composition according to claim 10, wherein the one or more oligomers having one or more ethylenically unsaturated groups are independently selected from urethane (meth)acrylate oligomers, polyester (meth) acrylate oligomers and epoxy (meth)acrylate oligomers.

12. The UV-curable composition according to claim 10, wherein the one or more oligomers having one or more ethylenically unsaturated groups are di- or trifunctional telechelic urethane (meth)acrylate oligomers with at least 4 urethane groups and a number average molecular weight (Mn) from 750-100000 g/mol.

13. The UV-curable composition according to claim 11, wherein the urethane (meth)acrylate oligomers is the reaction product of at least the following reactants:

(i) a hydroxy-functional backbone compound, (ii) an isocyanate compound; and (iii) a hydroxyl-functional end-capper further comprising a (meth)acrylate functional group;

wherein a molar ratio of the number of isocyanate groups in (ii) to the number of hydroxyl-groups in (i) in the urethane (meth)acrylate oligomer (b) is greater than 1.0.

14. The UV-curable composition according to claim 13, wherein the hydroxyl-functional backbone compound comprises a polyether, polyester, polybutadiene, polycarbonate, or silicone moiety.

15. The UV-curable composition according to claim 13, wherein the hydroxyl-functional backbone compound (i) comprises a polyether moiety.

16. The UV-curable composition according to claim 13, wherein the isocyanate compound (ii) comprises isophorone diisocyanate, 2,4-isomer toluene diisocyanate, 4,4'-methylenedicyclohexyl diisocyanate, 1,5-pentane diisocyanate, 2,2,4-trimethyl-hexamethylene diisocyanate, 2,4,4-trimethyl-hexamethylene diisocyanate, or hexamethylene diisocyanate, or a combination of any two or more thereof.

17. The UV-curable composition according to claim 13, wherein the hydroxyl-functional end-capper (iii) comprises hydroxyethyl (meth)acrylate, 2-hydroxypropyl (meth)acrylate, 3-hydroxypropyl (meth)acrylate, 4-hydroxybutyl (meth)acrylate, caprolactone (meth)acrylate, glycerol acrylate methacrylate, glycerol di(meth)acrylate, or a combination of any two or more thereof.

18. The UV-curable composition according to claim 10, wherein the one or more oligomers having one or more ethylenically unsaturated groups are present in the UV-curable composition in an amount of at least 45 wt. %, relative to the weight of the entire composition.

19. The UV-curable composition according to claim 10, wherein the one or more oligomers having one or more ethylenically unsaturated groups are present in the UV-curable composition in an amount of from 50 wt. % to 70 wt. % and the compound according to claim 1 is present in the UV-curable composition in an amount of from 25 wt. % to 45 wt. %, relative to the weight of the entire composition.

20. The UV-curable composition according to claim 10, wherein the photoinitiator (b) is present from 0.04 wt. % to 8 wt. % and comprises 2,4,6-trimethylbenzoylethoxyphenylphosphine oxide, 2,4,6-trimethylbenzoyldiphenylphosphine oxide, α-hydroxycyclohexyl phenyl ketone, 2-hydroxy-2-methyl-1-phenylpropanone, 2-hydroxy-2-methyl-1-(4-isopropylphenyl) propanone, 2-hydroxy-2-methyl-1-(4-dodecylphenyl) propanone, 2-Hydroxy-1-{4-[4-(2-hydroxy-2-methyl-propionyl)-benzyl]-phenyl}-2-methyl-propan-1-one, or 2-hydroxy-2-methyl-1-[(2-hydroxyethoxy)phenyl]propanone, or a combination of any two or more thereof.

21. The UV-curable composition according to claim 10, wherein the UV-curable composition is an optical fiber coating composition.

22. A method of preparing the compound of claim 1 or the composition or mixture according to claim 8, comprising:

(a) providing a cardanol, wherein the cardanol comprises a phenol group and an alkyl chain;

(b) alkoxylating the phenol group of the cardanol;

(c) subjecting the cardanol to a hydrogenation step, such that the alkyl chain is at least 93% hydrogenated; and (d) esterifying the cardanol with a (meth)acrylic acid to functionalize it with a single (meth)acrylate group;

wherein steps (b) and (c) are interchangeable.

* * * * *